United States Patent [19]

Van Agthoven

[11] Patent Number: 5,599,682
[45] Date of Patent: Feb. 4, 1997

[54] METHOD FOR THE PROTECTION OF LEUCOCYTES AND METHOD OF BLOOD ANALYSIS

[75] Inventor: André Van Agthoven, Marseille, France

[73] Assignee: Immunotech, Marseille, France

[21] Appl. No.: 246,239

[22] Filed: May 19, 1994

[30] Foreign Application Priority Data

May 19, 1993 [FR] France ................................. 93 06332

[51] Int. Cl.[6] ................................................. G01N 33/554
[52] U.S. Cl. ....................... 435/7.24; 435/7.25; 435/40.5; 435/374; 435/962; 436/17; 436/175; 436/176
[58] Field of Search ................................. 435/7.24, 7.25, 435/40.5, 240.1, 962; 436/17, 175, 176

[56] References Cited

FOREIGN PATENT DOCUMENTS

| | | |
|---|---|---|
| 0022670 | 1/1981 | European Pat. Off. . |
| 0161770 | 11/1985 | European Pat. Off. . |
| 0214613 | 3/1987 | European Pat. Off. . |
| 0530490 | 3/1993 | European Pat. Off. . |
| 8505640 | 12/1985 | WIPO . |

OTHER PUBLICATIONS

A. Boyem. "Isolation of Leucocytes from Human Blood.", Isolation of Leucocytes from Human Blood Further Observations., A One–stage Procedure for Isolation of Granulocytes and Lymphocytes from Human Blood., Isolation of Mononuclear Cells and Granulocytes from Human Blood., Isolation and Removal of Lymphocytes from Bone Marrow of Rats and Guinea–pigs. The Scandinavian Journal of Clinical and Laboratory Investigation. (1967–68. Suppl. 94–101. 305.293[B]).

*Primary Examiner*—James C. Housel
*Assistant Examiner*—Christopher L. Chin
*Attorney, Agent, or Firm*—Browdy and Neimark

[57] ABSTRACT

A method for protecting leukocytes in a blood sample, comprising contacting the blood sample with a preparation comprising an aliphatic aldehyde, a salt of an alkali metal or an alkaline earth metal, and optionally an agent to adjust isotonicity and hypotonically lysing erythrocytes in the blood sample.

7 Claims, 4 Drawing Sheets

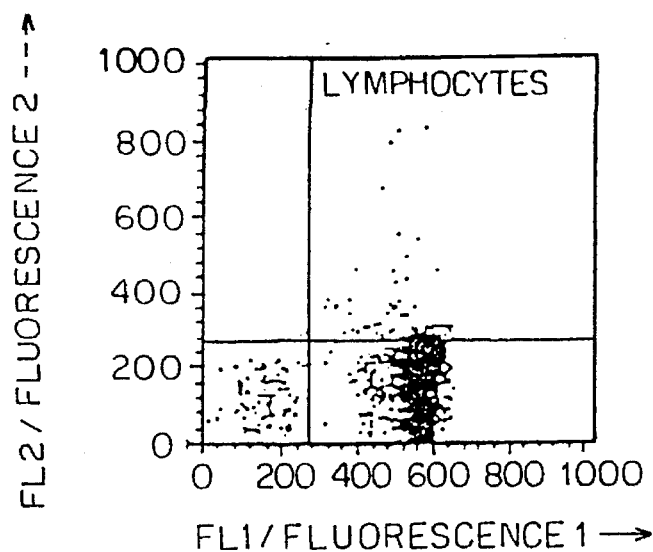
FIG.2d
FIG.2e
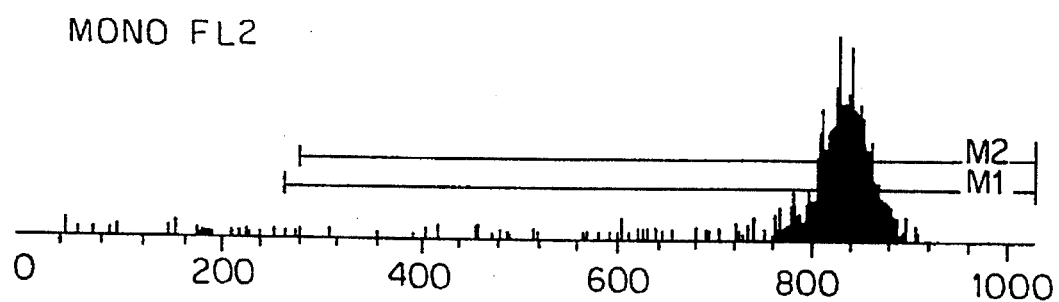

METHOD FOR THE PROTECTION OF LEUCOCYTES AND METHOD OF BLOOD ANALYSIS

FIELD OF THE INVENTION

The present invention concerns a method and a preparation for the protection of leucocytes, notably in a lysing procedure of erythrocytes, a preparation of protected blood and a method of blood analysis.

Blood contains several cell populations. The most numerous are the erythrocytes and the platelets which function in the exchange and the transport of carbon dioxide and oxygen. The platelets play a role in blood coagulation. The leucocytes are a minority population involved in the control of the immune system.

By microscopic analysis or by flow cytometric analysis, three subpopulations of leucocytes can be distinguished: polynuclear cells having several nuclei and mononuclear cells having only one nucleus. Among the mononuclear cells, lymphocytes can be distinguished by having a small spheric nucleus and monocytes, with a larger moon-shaped nucleus.

These populations can be distinguished by cytometry, in a scattergram. Of the leucocyte population, approximately 60% are polynuclear cells, approximately 30% are lymphocytes and 10% are monocytes.

Variations in the percentage of lymphocyte subpopulations can give an indication of the state of health of an individual.

By the staining of blood cells with monoclonal antibodies conjugated to a fluorescent marker, and after analysis of cells by microscopy or by flow cytometry, one can distinguish blood cells and subpopulations more precisely and in more detail than by simple optic means.

For instance, using the marker CD19, one can identify B-cells in the lymphocyte population which are derived from bone marrow. In the same population one can distinguish, with the CD3 marker, T-cells which are derived from the thymus. With the CD4 and CD8 markers one can distinguish T-cells with a helper function or a suppressor/killer function, respectively.

The identification of lymphocyte subclasses is important for the diagnosis and the treatment of diseases of the immune system.

Because the erythrocytes are a major population in the blood, they can mask leucocytes and make their analysis by flow cytometry difficult. Conventional immunofluorescence techniques include a physical separation of lymphocytes and erythrocytes, for instance by gradient density centrifugation (Boyem, A. 1968 Scand. J. Clin. Lab. Invest., 21 suppl. 97).

Another method, more rapid, is erythrocyte lysis in whole blood. For instance, in the method of Hansen (US-A-4.284.412, EP-A-0.022.670), a sample of blood treated with an anticoagulant is mixed with a fluorescent antibody conjugate preparation. After incubation and lysis of the erythrocytes, the sample is passed in a flow cytometer, to analyze leucocyte populations which are positive for a certain antibody.

To perform correct cytometric analysis, it is not only necessary to lyse all the erythrocytes; it is also necessary to conserve all the leucocytes in a morphological state in which the cytometer is capable of distinguishing between polynuclear cells, monocytes, lymphocytes, and the mixture of cellular debris and platelets. There is a great diversity of methods for lysing erythrocytes; these methods may be based, for instance, on acid treatment, alkaline treatment, treatment based on the use of ammonium chloride, polyhydric alcohol, or hypotonic shock. The problem with all these methods is, that by lysing the erythrocytes, modifications are introduced at the level of leucocyte morphology.

In the conventional methods, leucocyte degradation is prevented, for instance, by proceeding to the analysis immediately after the lysis, or by washing cells, or by the addition of a fixative such as formaldehyde or paraformaldehyde.

In the method of Chang (C. Chang, US-A-4.902.613, EP-A-0.161.770), the lysis is based on a hypotonic treatment in the presence of a polyhydric alcohol. During this lysis, the leucocytes are stabilized by the formaldehyde and by the salt of a weak acid. The inconvenience of this method is, that while lysing and fixing the cells simultaneously, complexes of erythrocyte debris and platelets of significant size are formed and interfere with the lymphocyte population in the scattergram. Additionally, the presence of polyhydric alcohols causes a displacement of monocytes in the scattergram, which in turn, might interfere with the lymphocyte population. Washing after the lysis improves the results of the scattergram by removing erythrocyte debris and platelets, and by a renaturation of the monocytes. The inconvenience of a washing step, disregarding the fact that it is time-consuming, is the loss of leucocytes. With the method described above, a loss of 20% to 40% of leucocytes in normal samples may be expected. This loss can be explained by the centrifugal force exerted on the cells, which are already partially denatured, and the interaction of certain cellular subpopulations with the wall of the tube; it may lead to an inaccurate cell count. This inconvenience may assume even larger proportions when it concerns leucocytes from subjects which have been affected by a disease, such as acquired immune deficiency syndrome (AIDS).

It would be desirable to find a procedure for the analysis of leucocytes which obviated the washing of samples as well as inaccuracies in the counting of leucocytes.

SUMMARY OF THE INVENTION

The object of the present application is a method and a preparation to protect leucocytes substantially from the denaturing effect of erythrocyte lysis and to inactivate platelets, preventing the formation of important sizeable aggregates with erythrocyte debris during the lysis, particularly the lysis by simple hypotonic shock. The method of protection, according to the present invention, is sufficiently efficient to guarantee good separation of leucocyte subpopulations in a scattergram obtained by flow cytometry. The fluorescent properties of the subpopulation, obtained by pre-labeling the cells with conjugated antibodies, are conserved during this procedure.

The object of the present application is a method to protect leucocytes, characterized by the treatment of the blood sample, which has been pre-treated with an anticoagulant, using a preparation which is substantially isotonic or hypertonic including:

an aliphatic aldehyde, a salt of an alkali metal or alkaline earth metal and a weak acid.

if necessary an agent for assuring isotonicity, and, more generally, a method to protect leucocytes, characterized herein that a blood sample, which has been treated previously with an anticoagulant, is treated with a preparation protecting leucocytes including a leucocyte-fixing reagent, prior to the hypotonic lysis of the erythrocytes.

The preparation described above will be called subsequently "isotonic preparation".

The aliphatic aldehyde in sufficient quantity leads to the fixation of all the cellular components of the blood. This fixation is obtained by a cross-linking of the amino-terminal groups of the proteins in the cell wall. Cells having a high protein density in the cell surface membrane, such as leucocytes and platelets, experience the highest degree of cross-linking, compared to the erythrocytes being which are cross-linked more weakly. This treatment makes cells with a high membrane protein density relatively resistant to a subsequent hypotonic lysis procedure.

By "aliphatic aldehyde" are meant aldehydes preferentially having one to four carbon atoms, for instance acetaldehyde, butyraldehyde, and glyoxal, and, notably, formaldehyde and paraformaldehyde.

The concentration of aliphatic aldehyde in the mixture of blood and the isotonic preparation is preferably between 0.036M and 1.8M and, preferably between 0.36M and 1.8M and, notably, between 0.36M and 0.72M. Below 0.36M (0.1% w/v), leucocyte protection is insufficient; above 1.8M, certain erythrocytes will not be lysed.

In the present application, the values for aliphatic aldehyde, notably formaldehyde, are indicated for a product which at 37% w/v is stabilized with 10% w/v of methanol (0.84M), as the one commercialized by the Merck Company. The quantities are expressed as total aldehyde.

Other reagents which fix leucocytes are, for instance, bifunctional reagents such as carbodiimide, succinic aldehyde, or Mirsky's reagent.

To conserve cellular morphology during the fixation procedure optimally and to reduce the size of the erythrocyte debris; the isotonic preparation, according to the invention, also contains the salt of an alkali metal or an alkaline earth metal and a weak acid, such as fumaric acid, malonic acid, succinic acid, citric acid, pyruvic acid, lactic acid, phosphoric acid, polyphosphoric acid, carbonic acid, and preferably formic acid and tartaric acid, and notably, those of the above-mentioned acids which form salts with alkaline earth metals which are soluble.

The alkali metal or alkaline earth metal is, for instance, lithium, sodium, potassium or magnesium and preferably the latter.

The concentration of the weak acid can be between 1 mM and 1M in the mixture of blood and the isotonic preparation. At a weak concentration of the order of 1 mM, the weak acid improves already the resolution of the cellular populations in the scattergram. Concentrations above 1 mM of a Weak acid may interfere with the subsequent hypotonic lysis. Its concentration is preferentially from 5 mM to 100 mM and, notably, from 10 to 50 mM.

By isotonic agent, a product or a preparation is meant, destined to be added in a quantity such that the final concentration of the preparation is close to a physiological value. The isotonic reagent, notably, does not interfere with the subsequent hypotonic lysis and should not lyse leucocytes. One could cite, for instance, notably mono- or dissacharides such as glucose and particularly saccharose.

The concentration of the isotonic agent should be such that the isotonic value of the mixture is adjusted to a value which is isotonic or hypertonic, preferably slightly hypertonic, to protect the cells during the fixation.

The adjustment of the acid concentration in the preparation is state of the art.

Before the lysing procedure, the duration of the contact between the sample and the preparation is, for instance, at least one minute, preferably at least 5 minutes and most preferred, at least, 10 minutes.

In any case, in view of the stability conferred to the preparation according to the invention, one may proceed to the lysing procedure at up to 30 minutes after the treatment.

Under the preferred conditions of the performance the above described method, the isotonic preparation includes also a small amount of a salt of a divalent cation other than the salt described above, notably of manganese or calcium, when the salt described above is a magnesium salt. The latter represents preferably approximately 5–15% of the molar concentration of the salt of the alkali metal or the alkaline earth metal and the weak acid, and most preferred approximately 8%. Notably the final concentration of calcium in the mixture of blood and the isotonic preparation is between 0.5 and 2.3 mM, and preferably between 1.1 and 1.6 mM.

In view of its weak concentration, the second salt can be the salt of either a weak acid, or of strong acid such as hydrochloric acid or sulphuric acid.

The object of the present invention is also a preparation for the protection of leucocytes characterized by the fact that it includes an aliphalic aldehyde, the salt of an alkali metal or an alkaline earth metal, if necessary an agent of isotonicity for making it substantially isotonic or hypertonic.

The preferred preparations are those which are defined in the proportions and the quantities described above. Especially preferred is a preparation which is an aqueous solution of approximately 1.22M in formaldehyde, approximately 37 mM in magnesium acetate, approximately 3 mM in calcium chloride, and at a pH of approximately 7.0. This preparation includes a sufficient amount of agent to achieve isotonicity; for instance, its saccharose concentration is approximately 40 mM. The volume of the isotonic preparation described above is 0.1 ml.

The object of the present application is also a preparation of protected blood, characterized herein that it includes a mixture of a blood sample treated with an anticoagulant and of an isotonic preparation defined above and including at least 0.036M of aliphatic aldehyde.

A method for counting leucocytes in a blood sample, using the method of protection according to the the invention, is notably the following, after which procedure lysis is obtained by hypotonic shock.

A sample of 0.1 ml of blood, treated with an anticoagulant is combined with a preparation of one or two fluorescent conjugated antibodies, preferably in a volume of 20 μl. After incubation, the isotonic preparation is added to the mixture. The isotonic preparation is particularly an aqueous solution of 1.22M of formaldehyde, 37 mM of magnesium acetate, 3 mM of calcium chloride, 40 mM of saccharose and has a pH of approximately 7.0. The volume of the isotonic preparation described above is 0.1 ml.

After combining, the mixture is shaken vigorously and left at room temperature for a 10 minute period. Subsequently, hypotonic erythrocyte lysis is obtained by the addition of 1 ml of distilled water. Lysis is considered to be total after 10 minutes at the end of which the sample is ready for cytometric analysis.

The entire procedure is performed preferably at room temperature (18°–24° C.).

Before cytometric analysis, the samples may be conserved for six hours at room temperature or for 48 hours at 4° C.

The method of the hypotonic lysis of whole blood has according to the experience of the applicant, a limitation with regard to the flow cytometric apparatus which is used.

The cytometers of Becton Dickinson and Co., for instance Facscan® or Facstar®, are well adapted to a lysis of this type. Other types of cytometers, based on a different optical system may give disappointing results; they are adapted to lysis under isotonic conditions. Therefore the object of the present application is also a method of analysing a leucocyte population of a blood sample in which a blood sample is treated with an anticoagulant, and then with an antibody, specific for at least one leucocyte population or subpopulation, followed by a fixing agent for leucocytes and subsequently is lysed hypotonically and the sample is analyzed by flow cytometry, characterized herein that after the treatment with the anticoagulant and, if desired, with at least one labeled antibody, the sample is treated using a preparation which is substantially isotonic or hypertonic including:

a fixing agent, which is an aliphatic aldehyde, a salt of an alkali metal or alkaline earth metal and a weak acid and, if necessary, an agent to obtain isotonicity, and then at least 1 minute after treatment of the sample with the preparation, which is substantially isotonic or hypertonic, one proceeds to the hypotonic lysis of said sample.

The above described method can notably be performed under the preferred conditions as explained above.

BRIEF DESCRIPTION OF THE INVENTION

FIG. 1 shows a result of a scatter analysis of a blood sample using the preparation of example 2 and subsequently submitting the sample to hypotonic lysis. The scattergram is obtained using a Facscan flow cytometer, commercialized by Becton Dickinson and Co. From left to right and from bottom to top, one notes good separation of the respective populations: platelets and erythrocyte debris, lymphocytes, monocytes and granulocytes. To study the lymphocytes, a threshold may be introduced to exclude the debris and the platelets and the lymphocytes can be defined in a region, as shown in the FIG. 1.

The FIGS. 2(a–h) represent a series of analyses on the Facscan cytometer of whole blood in the absence and in the presence of fluorescent marker antibodies and prepared by reaction with the stabilizing preparation according to the invention of example 2, and subsequent hypotonic lysis.

FIG. 2d represents a cytogram of whole blood (region R1), incubation in the presence of CD45-FITC and CD14-PE.

FIG. 2e represents a cytogram of whole blood (region R2), incubated in the presence of CD45-FITC and CD14-PE.

DETAILED DESCRIPTION OF THE INVENTION

Figure 1:
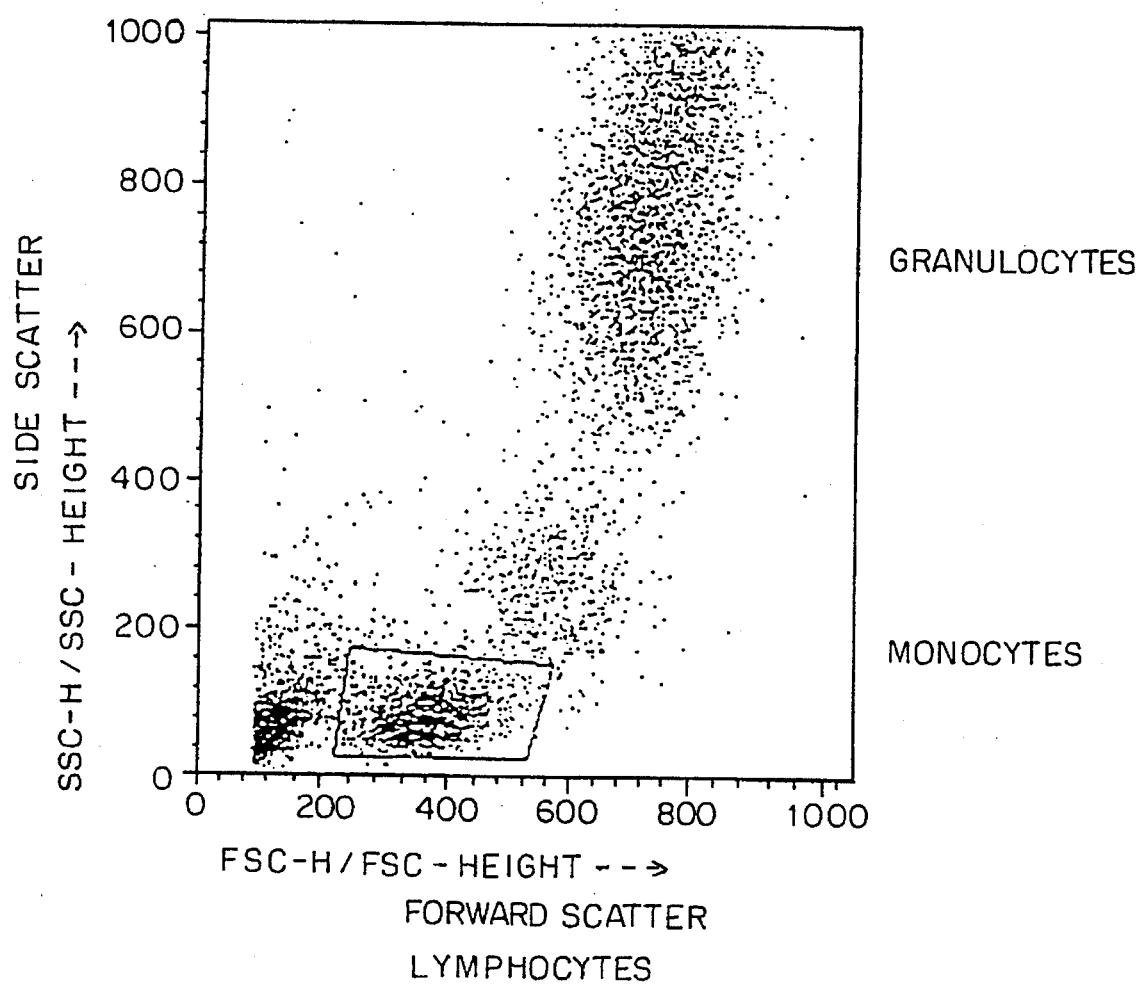
Figure 2A:
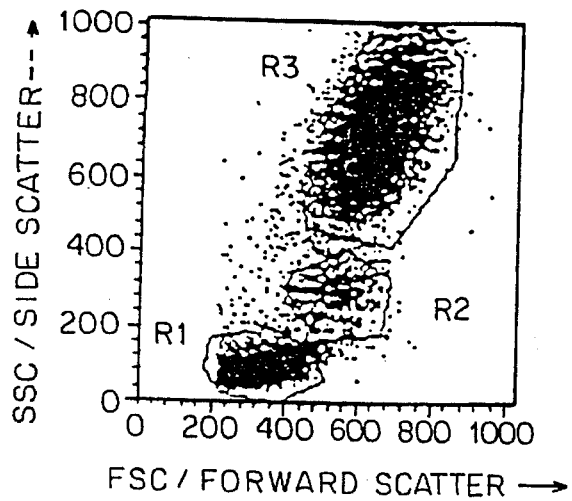
FIG. 2a represents a cytogram with a region of lymphocytes (R1), monocytes (R2) and granulocytes (R3).
Figure 2B:
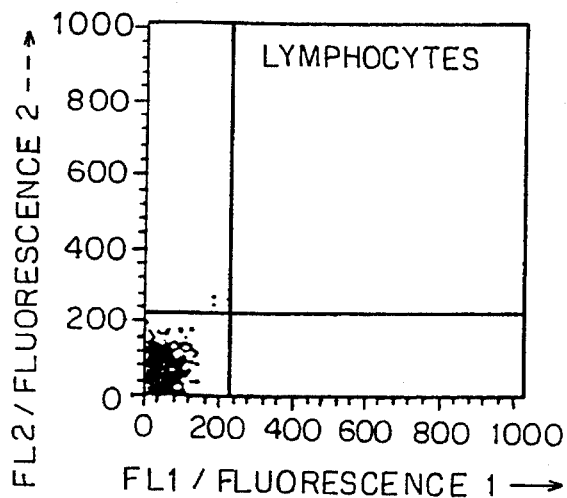
FIG. 2b represents a cytogram of whole blood (region R1) in the absence of fluorescent markers.
Figure 2C:
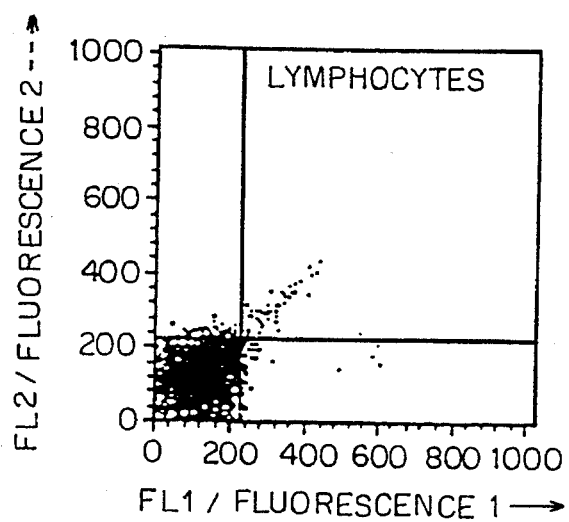
FIG. 2c represents a cytogram of whole blood (region R1) after incubation in the presence of isotypic control markers.
Figure 2F:
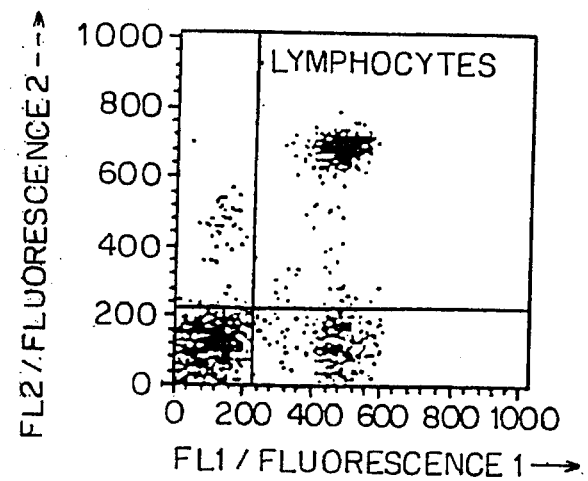
FIG. 2f represents a cytogram of whole blood (region R1) incubated in the presence of CD3-FITC and CD4-PE.
Figure 2G:
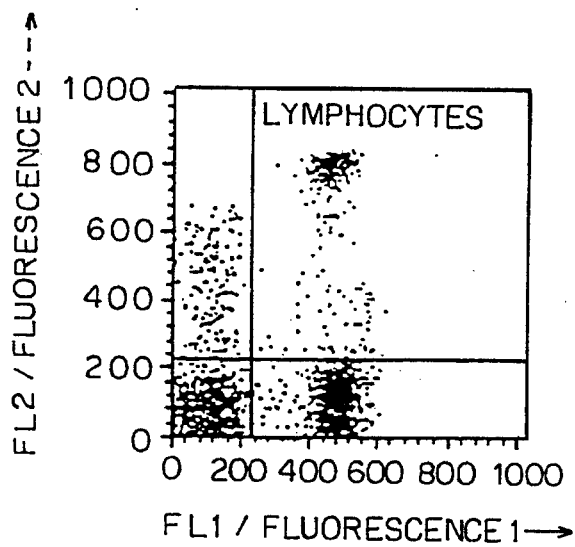
FIG. 2g represents a cytogram of whole blood (region R1), incubated in the presence of CD3-FITC and CDS-PE.
Figure 2H:
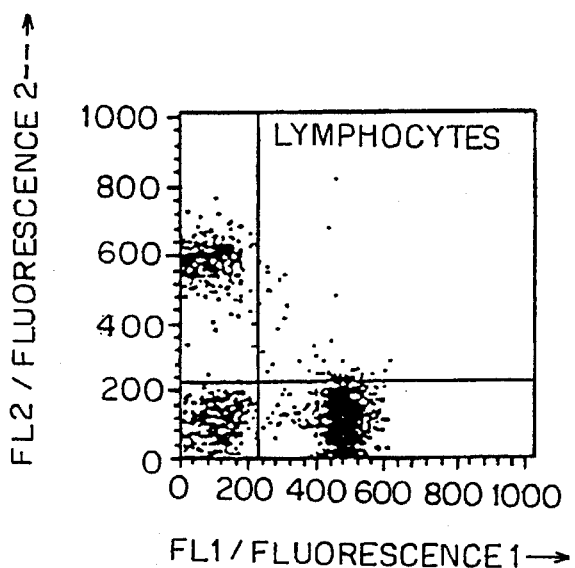
FIG. 2h represents a cytogram of whole blood (region R1), incubated in the presence of CD3-FITC and CD19-PE.

The following examples illustrate the present invention without., however, restricting it.

EXAMPLE 1: ISOTONIC PREPARATION

An isotonic aqueous preparation was prepared according to the invention and has the following composition:

| | |
|---|---|
| formaldehyde* | 0.206M |
| magnesium acetate | 0.037M |
| calcium chloride | 0.003M |
| saccharose | 0.04M |
| distilled water | |
| pH = 7.0 | |

*formaldehyde from a 37% w/v solution and stabilized with 10% w/v methanol.

EXAMPLE 2: ISOTONIC PREPARATION

An aqueous isotonic preparation was prepared according to the invention having the following composition:

| | |
|---|---|
| formaldehyde* | 0.1M |
| potassium, sodium tartrate | 0.06M |
| glucose | 0.1M |
| distilled water | |
| pH = 7.0 | |

*formaldehyde from a 37% w/v solution and stabilized in 10% w/v methanol.

EXAMPLE 3: ISOTONIC PREPARATION

An aqueous isotonic preparation was established according to the invention, having the following compostion:

| | |
|---|---|
| formaldehyde* | 0.185M |
| sodium polyphosphate | 1% w/v |
| saccharose | 20 mM |
| sodium carbonate | 10 mM |
| distilled water | |
| pH = 7.0 | |

*formaldehyde from a 37% w/v solution and stabilized with 10% w/v methanol.

EXAMPLE 4: ANALYSIS OF A BLOOD SAMPLE

Samples of 0.1 ml of blood, treated with an anticoagulant, are distributed in 6 tubes.

To tube 1, 20 µl of PBS is added.

To tube 2, 20 µl of a mixture of two monoclonal antibodies is added (isotypic controls) with an irrelevant specificity, one conjugated to isothiocyanate (FITC) Cat. No. 0639 (10 µl), the other to phycoerythrin cat.#0670 (2 µl) and PBS (8 µl) are added.

To tube 3, 20 µl of a mixture of monoclonal antibodies having a CD45 specificity conjugated to FITC, cat.#0782 (2 µl), and of a monoclonal antibody with a CD14 specificity conjugated to phycoerythrin cat.#0650 (2.5 µl) and PBS (15.5 µl) are added.

To tube 4, 20 µl of a mixture of monoclonal antibodies with a CD3 specificity conjugated to FITC cat.#1281 (2 µl), and an antibody with a CD4 specificity conjugated to PE cat.#0449 (10 µl) and PBS (8 µl) are added.

To tube 5, 20 µl of a mixture of CD3-FITC cat.#1281 (2 µl), and CD8-PE antibodies cat.#0452 (3.3 µl) and PBS (14.7 µl) are added.

To tube 6, 20 μl of a mixture of antibodies CD3-FITC cat.#1281 (2 μl), CD19-PE antibody cat.#1285 (10 μl) and PBS (8 μl) are added.

The above mentioned antibodies are commercialized by Immunotech SA, in its product range "IOTEST". Comparable antibodies are commercialized by other companies.

After 20 minutes of incubation with the antibodies, 0.1 ml of the preparation of example 1 is added and the tubes are vortexed immediately. After 10 minutes of reaction, a volume of 1 ml of distilled water is added to the tubes and the tubes are vortexed immediately.

After two hours at room temperature, the samples are analyzed by flow cytometry with a Facscan cytometer from Becton Dickinson and Co. In the scatter analysis, a threshold is used to prevent counting of debris and platelets. A region is created around the populations of lymphocytes, monocytes and granulocytes. A fluorescence 1 analysis, detecting FITC-conjugates and fluorescence 2 analysis, detecting PE-conjugates is effected on the lymphocyte cells in the region. Cells, positive in fluorescence for CD45, represent the leucocytes, permitting the distinction between leucocytes and debris plus platelets. Cells, positive for CD14, are monocytes permitting the distinction between monocytes and lymphocytes; cells positive for CD3 and CD4 are helper T-cells. Cells positive for CD3 and CD4 are cytotoxic suppressor T-cells; cells positive for CD19 are B-cells.

The results are presented in FIGS. 2.

It is observed that in the lymphocyte region, 97% of the events represent lymphocytes, 68% represent T-cells, 17% represent B-cells and 15% represent neither T nor B-cells.

In the T-cell population, 53% are helper cells and 16% are cytotoxic/suppressor cells.

In the monocyte region, 96% of the events represent monocytes.

CONCLUSION

From the analysis of FIG. 1 it may be concluded that the leucocyte populations and the debris are clearly separated in the scattergram.

FIG. 2 demonstrates that the method, according to the present invention, conserves the fluorescent properties of the labeled cells and that good cellular discrimination is obtained using whole blood.

Parallel comparisons with the Facslyse method of Becton Dickinson and Co. shows that, using the present invention, substantially, identical values are obtained.

I claim:

1. A method for protecting leucocytes in a blood sample which has been pre-treated with an anticoagulant comprising:
   adding to said blood sample a protective preparation which is substantially isotonic or hypertonic, said preparation comprising:
   an aliphatic aldehyde,
   a salt of an alkali metal or an alkaline earth metal, and optionally, an agent to adjust isotonicity; and
   hypotonic lysing erythrocytes in the blood sample.

2. A method according to claim 1, wherein the sample is treated with at least one-antibody specific for a subpopulation of lymphocytes before the treatment using the protective preparation.

3. A method according to claim 2 wherein the lysis is performed at least one minute after mixing the sample with the protective preparation.

4. A method according to claim 1 wherein the lysis is performed at least one minute after mixing the sample with the protective preparation.

5. A method for analyzing the leucocyte population of a blood sample comprising:
   treating said blood sample with an anticoagulant;
   treating said blood sample with a protective preparation which is substantially hypertonic or isotonic, said preparation comprising:
   a fixative which is an aliphatic aldehyde,
   a salt of an alkali metal or an alkaline earth metal and a weak acid,
   an optional agent to render the preparation isotonic; and
   at least one minute after the blood sample has been treated, lysing said sample under hypotonic conditions.

6. A method according to claim 5, characterized herein insofar as the sample is treated with at least one antibody specific for a subpopulation of lymphocytes before the treatment using the protective preparation.

7. A method according to claim 6 wherein the lysis is performed at least one minute after mixing the sample with the protective preparation.

* * * * *